United States Patent [19]

Billotti

[11] Patent Number: 5,785,673

[45] Date of Patent: Jul. 28, 1998

[54] KNEE BRACE WITH SECURE ATTACHMENT

[76] Inventor: Joseph D. Billotti, 18 Powder Hill, Saddle River, N.J. 07458

[21] Appl. No.: 762,749

[22] Filed: Dec. 10, 1996

Related U.S. Application Data

[63] Continuation-in-part of Ser. No. 587,846, Jan. 11, 1996, Pat. No. 5,582,584.

[51] Int. Cl.$^6$ ........................................................ A61F 5/00
[52] U.S. Cl. .......................... 602/26; 602/13; 128/DIG. 20
[58] Field of Search ................................ 602/5, 13, 23, 602/26, 62–64; 128/DIG. 20, DIG. 15

[56] References Cited

U.S. PATENT DOCUMENTS

| | | |
|---|---|---|
| 2,823,668 | 2/1958 | Van Court et al. . |
| 3,853,123 | 12/1974 | Moore . |
| 3,955,565 | 5/1976 | Johnson, Jr. . |
| 4,084,584 | 4/1978 | Detty . |
| 4,219,892 | 9/1980 | Rigdon . |
| 4,263,905 | 4/1981 | Couch, Jr. . |
| 4,280,489 | 7/1981 | Johnson, Jr. . |
| 4,378,009 | 3/1983 | Rowley et al. . |
| 4,508,112 | 4/1985 | Seeler . |
| 4,597,384 | 7/1986 | Whitney . |
| 4,628,918 | 12/1986 | Johnson, Jr. . |
| 4,628,945 | 12/1986 | Johnson, Jr. . |
| 4,669,455 | 6/1987 | Bellatti . |
| 4,703,750 | 11/1987 | Sebastian et al. . |
| 4,730,610 | 3/1988 | Graebe . |
| 4,872,448 | 10/1989 | Johnson, Jr. . |
| 4,926,884 | 5/1990 | Lonardo . |
| 4,938,207 | 7/1990 | Vargo . |
| 4,953,569 | 9/1990 | Lonardo . |
| 4,961,418 | 10/1990 | McLaurin-Smith . |
| 5,113,877 | 5/1992 | Johnson, Jr. et al. . |
| 5,125,400 | 6/1992 | Johnson, Jr. . |
| 5,230,695 | 7/1993 | Silver et al. . |
| 5,288,286 | 2/1994 | Davis et al. . |
| 5,378,224 | 1/1995 | Billotti . |
| 5,582,584 | 12/1996 | Billotti . |

*Primary Examiner*—Linda C. Dvorak
*Attorney, Agent, or Firm*—Arthur Jacob

[57] ABSTRACT

A brace for supporting a weakened knee joint wherein lower and upper anchor bands are carried by a sleeve for location upon and attachment to the lower leg and the upper leg adjacent the knee joint, with essentially inextensible support straps following respective helical paths around the knee joint between the lower and upper anchor bands, and inflatable elements juxtaposed with the lower and upper anchor bands which subsequently are inflated to anchor the attached lower and upper anchor bands in place for firm and accurate securement upon installation in the desired location and for maintaining the desired location during use.

15 Claims, 10 Drawing Sheets

KNEE BRACE WITH SECURE ATTACHMENT

This application is a continuation-in-part of application Ser. No. 08/587,846, filed Jan. 11, 1996, now U.S. Pat. No. 5,582,584.

The present invention relates generally to braces for supporting joints of the body and pertains, more specifically, to a knee brace having a secure attachment to the leg adjacent the knee being supported and a method for attaching the knee brace to the leg accurately, securely and with increased ease.

A large variety of braces has been made available for the support of body joints which have become weakened as a result of sports activity, accident, deterioration due to age, or disease. Braces for the knee are designed primarily to provide support while enabling the knee to function during normal activity. An important aspect in assuring proper operation of a knee brace is the ability of the brace to be secured in proper relation to the knee and to remain in place during use.

The present invention provides a brace which not only establishes the desired support for a weakened knee, but enables secure placement with increased accuracy, reliability, ease and comfort. As such, the present invention attains several objects and advantages, some of which are summarized as follows: Provides effective support to a weakened knee with minimal interference with the functioning of the knee during normal activity; enables increased ease of placement and securement in appropriate position in relation to the knee, with increased accuracy of placement; provides a secure attachment to the leg for maintaining the brace accurately in place during use; enables ease of attachment and detachment through simplified multiple steps for encouraging proper use; attains a higher degree of comfort both during installation and during use, with ease of adjustment to maintain proper placement as well as comfort; enables ease of storage and transportation, as well as ready proper placement and securement in place; provides a simplified construction which is economical to manufacture and attains reliable performance over an extended service life.

The above objects and advantages, as well as further objects and advantages, are attained by the present invention which may be described briefly as a brace to be attached to an upper leg and a lower leg of a body for supporting a weakened knee joint located between the upper leg and the lower leg, the brace comprising: a sleeve of resilient material for fitting over the knee joint, the sleeve having a lower tubular portion for extending over the lower leg adjacent the knee joint, an upper tubular portion for extending over the upper leg adjacent the knee joint, and an intermediate tubular portion for extending over the knee joint when the sleeve is fitted over the knee joint; a lower securing element attached to the lower tubular portion of the sleeve; a lower anchor band attached to the lower tubular portion of the sleeve and extending in a lateral direction between opposite band ends for being located at a location along the lower tubular portion of the sleeve, the lower anchor band including lower band securing means for securing the lower anchor band to the lower securing element in the location along the lower tubular portion of the sleeve; a lower front support attached to the lower tubular portion of the sleeve, the lower front support extending in the lateral direction between opposite support ends and having a laterally extending upper edge and an opposite laterally extending lower edge spaced altitudinally from the upper edge; a first strap integral with the lower front support adjacent the upper edge, the first strap projecting from the lower front support upwardly at an acute angle to the lateral direction to extend generally toward the upper tubular portion of the sleeve; a first guide band attached to the sleeve and guiding the first strap along a first helical path around the sleeve; an upper securing element attached to the upper tubular portion of the sleeve; a first upper anchor band integral with the first strap and spaced away from the upper edge of the lower front support, the first upper anchor band extending laterally for being located at a first location along the upper tubular portion of the sleeve, adjacent the intermediate portion of the sleeve, and including first upper anchor band securing means for securing the first upper anchor band to the upper securing element in the first location along the upper tubular portion of the sleeve, with the first strap following the first helical path; a second strap integral with the lower front support adjacent the upper edge and projecting from the lower front support upwardly at an acute angle to the lateral direction to extend generally toward the upper tubular portion of the sleeve; a second guide band attached to the sleeve and guiding the second strap along a second helical path around the sleeve, the second helical path being opposite to the first helical path; a second upper anchor band integral with the second strap and spaced away from the upper edge of the lower front support, the second upper anchor band extending laterally for being located at a second location along the upper tubular portion of the sleeve, adjacent the intermediate portion of the sleeve, and including second upper band securing means for securing the second upper anchor band to the upper securing element at the second location along the upper tubular portion of the sleeve, with the second strap following the second helical path; lower inflatable means attached to the lower tubular portion of the sleeve in position for being overlapped by the lower anchor band when the lower anchor band is secured to the lower securing element in the location along the lower tubular portion of the sleeve, the lower inflatable means being selectively inflatable when the lower tubular portion of the sleeve and the lower anchor band are located over the lower leg to grip the lower leg and anchor the lower anchor band to the lower leg; and upper inflatable means attached to the upper tubular portion of the sleeve in position to be overlapped by the first and second upper anchor bands when the first and second upper anchor bands are secured to the upper securing element in the respective first and second locations along the upper tubular portion of the sleeve, the upper inflatable means being selectively inflatable when the upper tubular portion of the sleeve and the first and second upper anchor bands are located over the upper leg to grip the upper leg and anchor the first and second upper anchor bands to the upper leg; the first and second straps being essentially inextensible such that upon anchoring the lower anchor band to the lower leg, the first upper anchor band to the upper leg and the second upper anchor band to the upper leg, with the first and second straps following the respective first and second helical paths, the first and second straps support the weakened knee joint.

The invention will be understood more fully, while still further objects and advantages will become apparent, in the following detailed description of preferred embodiments of the invention illustrated in the accompanying drawing, in which.

Figure 1:
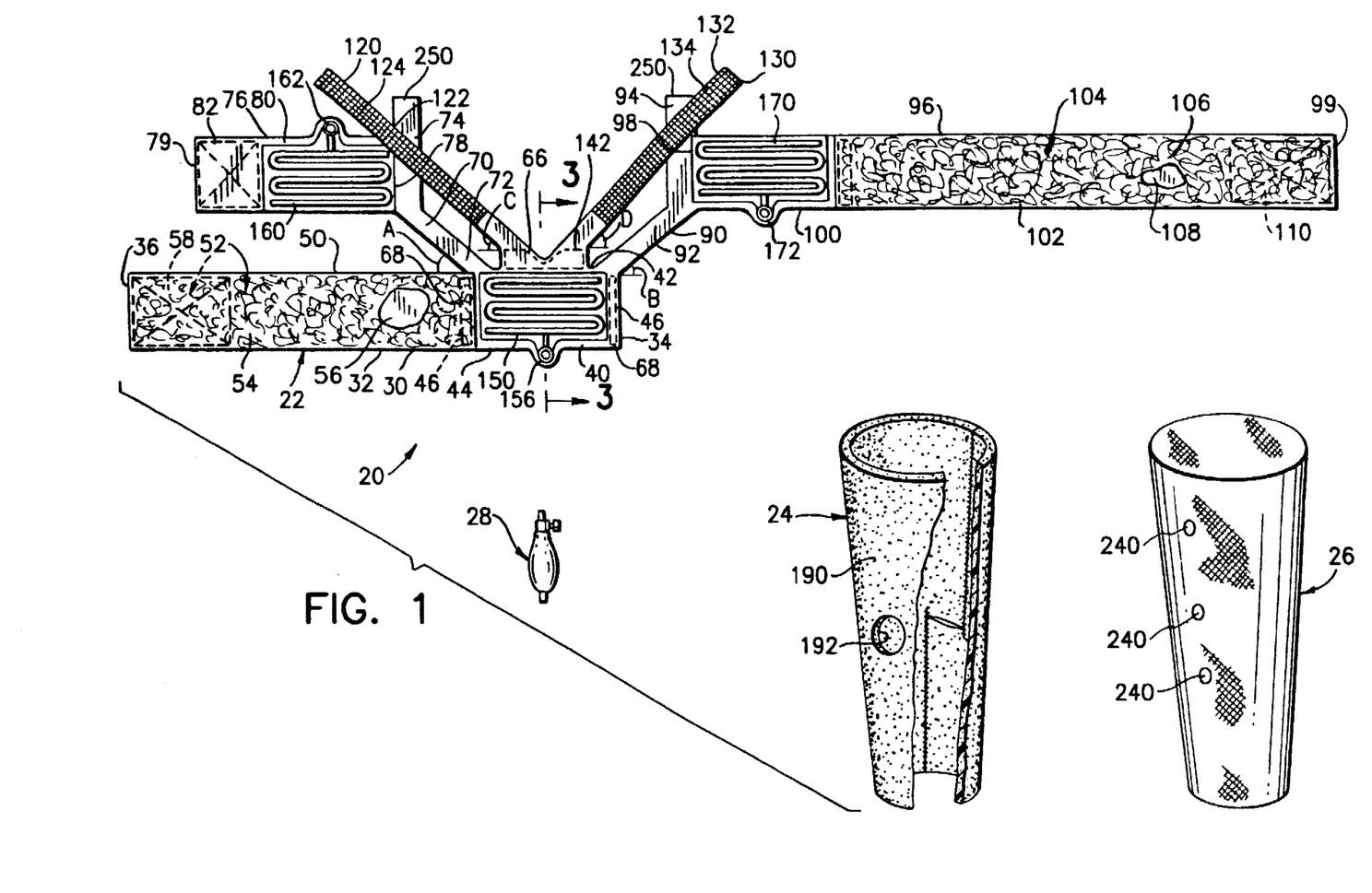
FIG. 1 is a pictorial illustration of component parts of a knee brace constructed in accordance with the present invention, including a front elevational view of the support component of the knee brace.
Figures 2, 3:
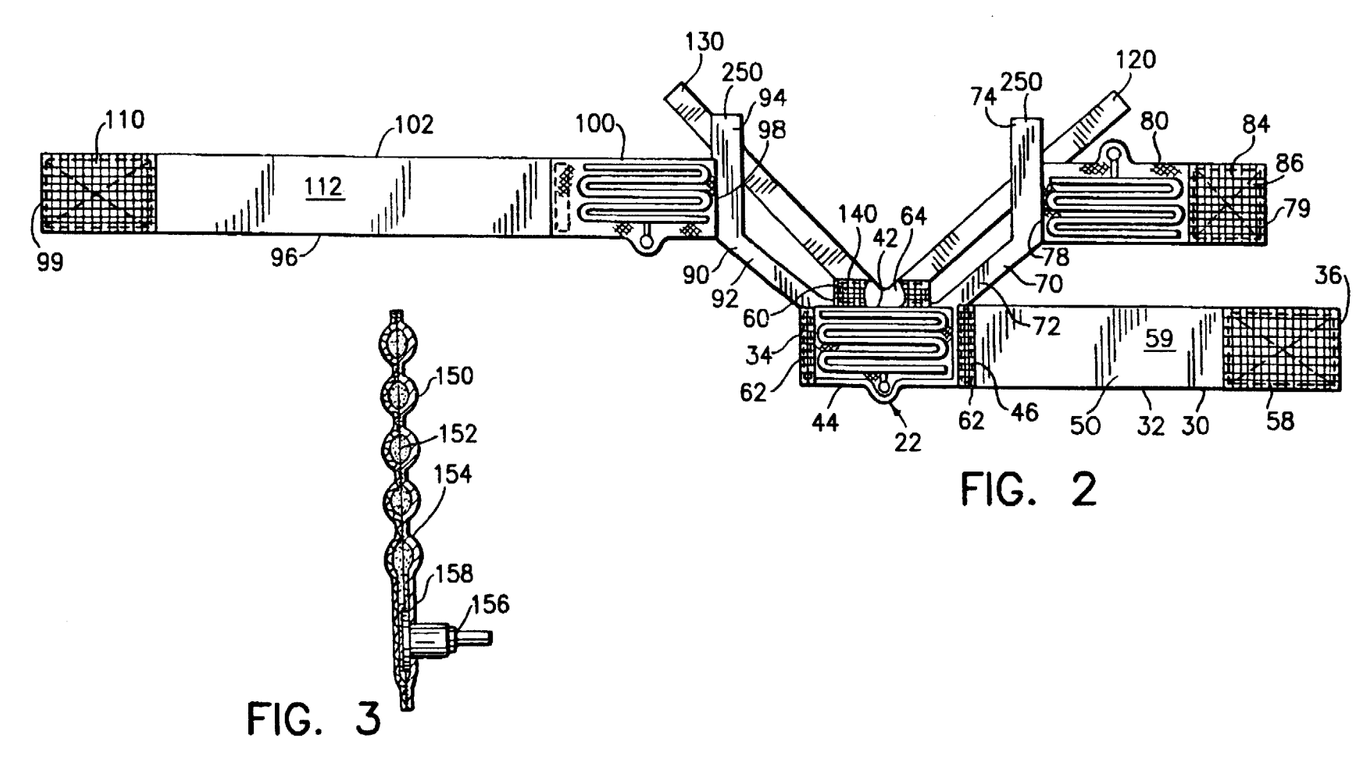
FIG. 2 is a rear elevational view of the support component.
FIG. 3 is an enlarged cross-sectional view taken along line 3—3 of FIG. 1.

Referring now to the drawing, and especially to FIGS. 1 and 2 thereof, a knee brace constructed in accordance with the present invention is illustrated at 20 and is seen to include a support component 22, an inner sleeve 24, and an outer sleeve 26. An air pump 28 is an additional component part utilized in connection with the knee brace 20, as will be explained in detail below.

Support component 22 includes a member 30 in the form of a relatively thin sheet of flexible and essentially inextensible synthetic polymeric material, such as a commercially available nylon fabric coated on one side with a polyurethane film, the term "essentially inextensible" meaning that the material resists stretching in response to tensile loads, while remaining flexible. Member 30 includes a lower anchor band 32 extending in a lateral direction between opposite ends 34 and 36. A lower front segment 40 of the lower anchor band 32 extends laterally from the end 34 toward the end 36 and has a laterally extending upper edge 42, an opposite laterally extending lower edge 44 spaced altitudinally from the upper edge 42, and laterally opposite side edges 46. Lower anchor band 32 includes securing means in the form of a securing segment 50 extending laterally from the lower front segment 40 to the end 36 and carrying a hook-and-loop fastener 52 having an elongate loop element 54, extending along a front face 56 of the securing segment 50 from the lower front segment 40 to the end 36, and a hook element 58 extending along a rear face 59 of the securing segment 50 from the end 36 toward the lower front segment 40. A suitable hook-and-loop fastener is available under the trademark VELCRO.

Locator means are placed at upper edge 42 and at each side edge 46 of the lower front segment 40 and are shown in the form of hook elements 60 and 62 of a hook-and-loop fastener, the hook elements 60 and 62 being affixed to the lower front segment 40, at a rear face 64 thereof, along the upper edge 42 and along the opposite side edges 46, as by sewing at 66 and at 68, respectively, or otherwise permanently attaching the hook elements 60 and 62 to the lower front segment 40.

A first strap 70 is integral with the lower front segment 40 of the lower anchor band 32 adjacent the upper edge 42 and projects from the lower front segment 40 at an acute angle A to the lateral direction to extend generally toward the end 36 of the lower anchor band 32. First strap 70 includes an intermediate segment 72 extending along the direction of angle A, and a terminal segment 74 extending in an altitudinal direction, generally parallel to side edges 46 and normal to the upper edge 42. A first upper anchor band 76 is integral with the first strap 70 and is spaced away from the upper edge 42 of the lower front segment 40 of the lower anchor band 32 by an altitudinal distance determined by the length of the intermediate segment 72 and the angle A, the first upper anchor band 76 extending laterally, generally parallel to the lower anchor band 32, between opposite ends 78 and 79. First upper anchor band 76 includes a first upper front segment 80 extending laterally from the end 78, at the terminal segment 74, toward the end 79 and securing means in the form of a securing segment 82 extending laterally from the first upper front segment 80 to the end 79 and carrying a hook element 84 of a hook-and-loop fastener, the hook element 84 extending along a rear face 86 of the securing segment 82 from the end 79 toward the first upper front segment 80.

A second strap 90 is integral with the lower front segment 40 of the lower anchor band 32 adjacent the upper edge 42 and projects from the lower front segment 40 at an acute angle B to the lateral direction to extend generally toward the end 34 of the lower anchor band 32. Second strap 90 includes an intermediate segment 92 extending along the direction of angle B, and a terminal segment 94 extending in an altitudinal direction. A second upper anchor band 96 is integral with the second strap 90 and is spaced away from the upper edge 42 of the lower front segment 40 of the lower anchor band 32 by an altitudinal distance determined by the length of the intermediate segment 92 and the angle B, the second upper anchor band 96 extending laterally, generally parallel to the lower anchor band 32, between opposite ends 98 and 99. Second upper anchor band 96 includes a second upper front segment 100 extending laterally from the end 98, at the terminal segment 94, toward the end 99 and securing means in the form of a securing segment 102 extending laterally from the second upper front segment 100 to the end 99 and carrying a hook-and-loop fastener 104 having an elongate loop element 106, extending along a front face 108 of the securing segment 102 from the front segment 100 to the end 99, and a hook element 110 extending along a rear face 112 of the securing segment 102 from the end 99 toward the second upper front segment 100. A suitable hook-and-loop fastener is available under the trademark VELCRO. Thus, the first and second straps 70 and 90 are in a V-shaped array, radiating from the upper edge 42 of the lower front segment 40 of the lower anchor band 32.

A first auxiliary strap 120 is integral with the lower front segment 40 of the lower anchor band 32, adjacent the upper edge 42 thereof, and projects from the lower front segment 40 at an acute angle C to the lateral direction to extend generally toward end 36 of the lower anchor band 32. First auxiliary securing means are shown in the form of a securing segment 122 extending along the first auxiliary strap 120 and carrying a hook element 124 of a hook-and-loop fastener. A second auxiliary strap 130 is integral with the lower front segment 40 of the lower anchor band 32, adjacent the upper edge 42 thereof, and projects from the lower front segment 40 at an acute angle D to the lateral direction to extend generally toward end 34 of the lower anchor band 32. Second auxiliary securing means are shown in the form of a securing segment 132 extending along the second auxiliary strap 130 and carrying a hook element 134 of a hook-andloop fastener. Thus, the first and second auxiliary straps 120 and 130 are in a V-shaped array, located between the V-shaped array followed by the first and second straps 70 and 90.

In the embodiment illustrated in FIGS. 1 through 12 of the drawing, the first and second straps 70 and 90 are constructed unitary with the lower front segment 40, while the auxiliary straps 120 and 130 are affixed to a tab 140 constructed unitary with the lower front segment 40, as by sewing at 142 or otherwise joining the auxiliary straps 120 and 130 with the tab 140 to render the auxiliary straps 120 and 130 integral with the lower front segment 40.

As best seen in FIG. 3, as well as in FIGS. 1 and 2, the lower anchor band 32 includes inflatable means in the form of bladder 150 in the lower front segment 40 of the lower anchor band 32, the bladder 150 having a sinuous internal passage 152 established by affixing a bladder sheet 154 to the sheet material of member 30 at the lower front segment 40, along a sinuous pattern, as by laminating or welding the bladder sheet 154 to the member 30 along the sinuous pattern, to construct the passage 152. A valve 156 communicates with the passage 152 of the bladder 150, through a feed passage 158, and normally closes communication to the bladder 150. Selective opening of the valve 156 enables access to the passage 152 of the bladder 150 for selectively inflating and deflating the bladder 150, to alternately expand and contract the lower front segment 40 in directions normal to the lateral and altitudinal directions; that is, normal to the plane of the paper in FIGS. 1 and 2.

Similarly, first upper anchor band 76 includes inflatable means in the form of a bladder 160 located in first upper front segment 80 and constructed in the manner described above in connection with bladder 150 for selective inflation and deflation through a valve 162. Likewise, second upper anchor band 96 includes inflatable means in the form of a bladder 170 located in second upper front segment 100 and constructed in the manner described above in connection with bladder 150 for selective inflation and deflation through a valve 172.

Turning now to FIGS. 4 through 8, knee brace 20 is applied to a knee 180 as follows: First, inner sleeve 24 is slipped over the knee 180 to extend along the adjacent upper leg 182 and lower leg 184. To this end, inner sleeve 24 is constructed of a pliable and somewhat stretchable material, the material providing an outer surface 190 having surface characteristics which allow the attachment of a hook element of a hook-and-loop fastener to the outer surface 190, for purposes to be described in detail hereinafter. The preferred material for inner sleeve 24 is a commercially available material having a core of closed-cell foam rubber laminated with an inner layer of stretchable nylon material and an outer layer of nylon material rendered compatible with a VELCRO fastener element. One such material is available from Rubatex Company located in Bedford, Virginia. When in place, the inner sleeve 24 fits snugly over the knee 180, and an opening 192 in the inner sleeve 24 provides clearance for the patella of the knee 180.

Figure 4:
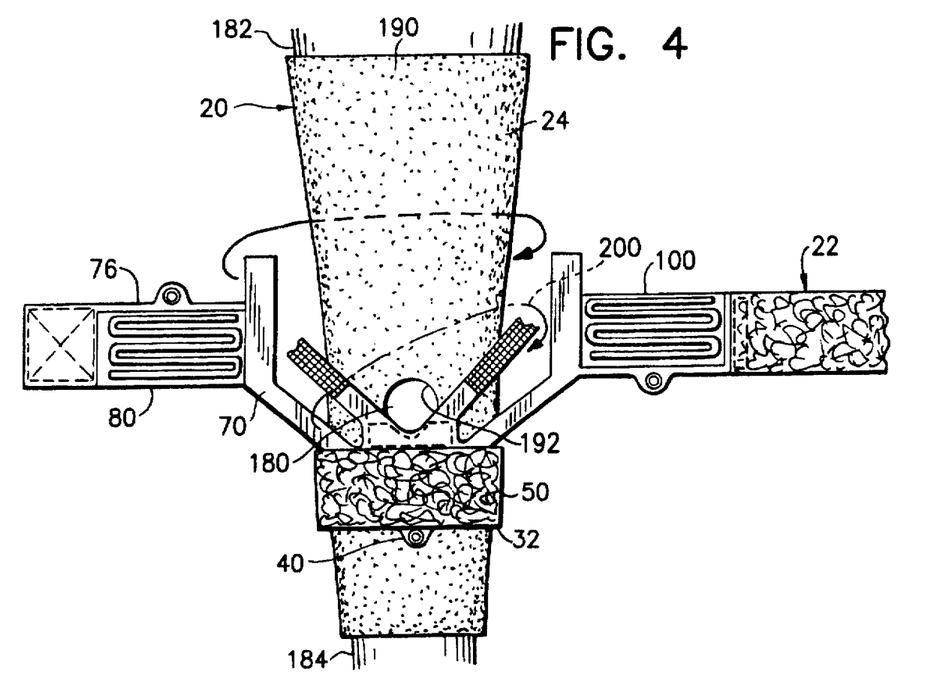
FIGS. 4 through 10 are elevational views illustrating various stages of attachment of the knee brace.

Once the inner sleeve 24 is fitted over the knee 180, as described above, the support component 22 is placed over the inner sleeve 24 as follows: The lower front segment 40 of the lower anchor band 32 is located along the anterior of the lower leg 184 and is held in place by the hook elements 60 at the upper edge 42 and the hook elements 62 at the side edges 46 of the lower front segment 40, which hook elements 60 and 62 grasp the material of the inner sleeve 24 along outer surface 190 to hold the lower front segment 40 in place for completion of the next step. Then, the securing segment 50 is wrapped around the lower leg 184 and over the lower front segment 40, and the hook element 58 is engaged with the loop element 54 of the hook-and-loop fastener 52 to secure the lower anchor band 32 in place.

Figure 5:
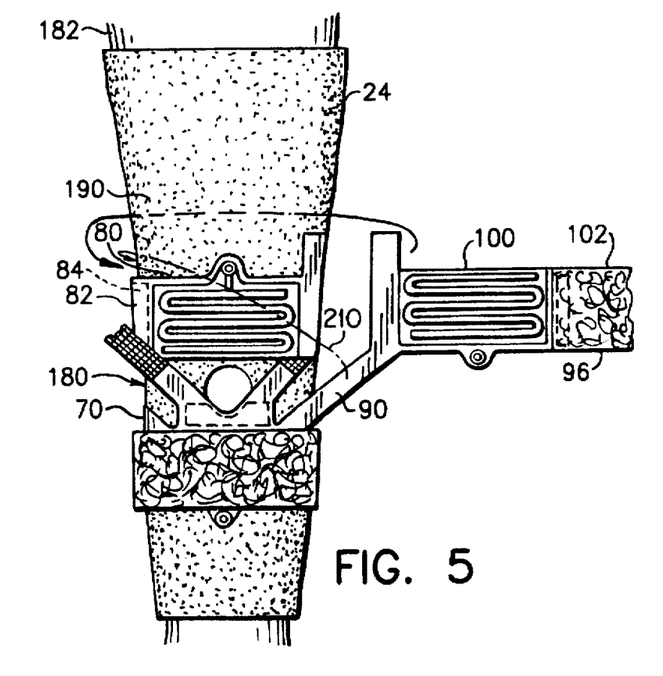
Figures 6, 7:
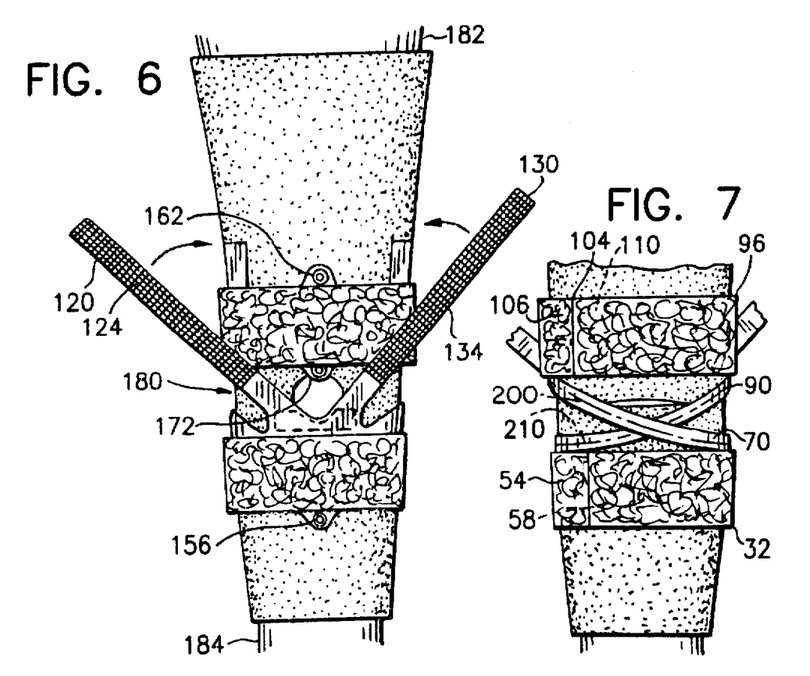

Next, the first strap 70 is wound along a first helical path 200, as seen in FIG. 4, with the helical path 200 extending behind the knee 180, as seen in FIG. 7, the first upper front segment 80 of the first upper anchor band 76 is placed along the anterior of the upper leg 182 and the securing segment 82 of the first upper anchor band 76 is located upon the upper leg 182, where the first upper anchor band 76 is secured in place, overlying the inner sleeve 24, by attaching the hook element 84 of the securing segment 82 to the outer surface 190 of the inner sleeve 24, as seen in FIG. 5.

Then, the second strap 90 is wound along a second helical path 210, as seen in FIG. 5, with the second helical path 210 extending behind the knee 180, as seen in FIG. 7, the second upper front segment 100 of the second upper anchor band 96 is placed along the anterior of the upper leg 182, overlying the first upper front segment 80, and the securing segment 102 of the second upper anchor band 96 is wrapped around the upper leg 182, over the first upper anchor band 76, to engage the hook element 110 of the second upper anchor band 96 with the loop element 106 of the hook-and-loop fastener 104, thereby securing the second upper anchor band 96 in place, overlying the first upper anchor band 76 and the inner sleeve 24, as seen in FIGS. 6 and 7. The length of the second upper anchor band 96 between the ends 98 and 99 is somewhat greater than the corresponding length of the lower anchor band 32 between the ends 34 and 36 in order to accommodate the greater girth of the upper leg 182, as compared to the lesser girth of the lower leg 184. Note that the placement of the front segments 40, 80 and 100 locates the valves 156, 162 and 172 essentially aligned longitudinally along the anterior of the upper and lower legs 182 and 184, as illustrated in FIG. 8 and exposes each valve for purposes to be described below.

Figure 8:
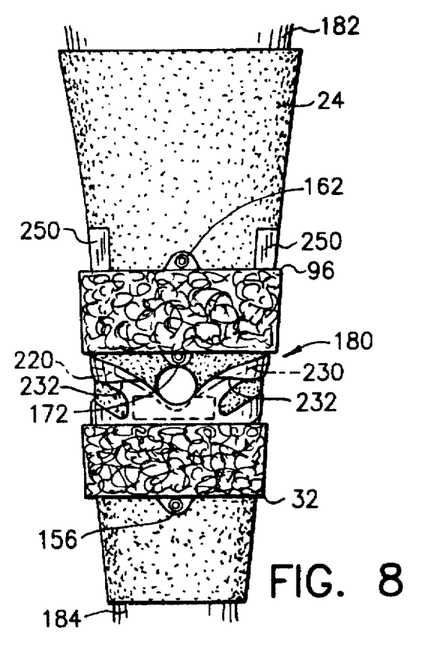
Figure 9:
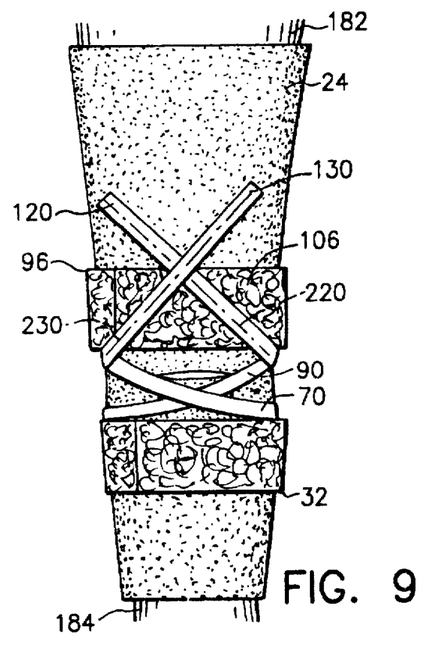

Next, the auxiliary straps 120 and 130 are wound around the knee 180, along respective helical paths 220 and 230, as illustrated in FIGS. 6 through 8, and are secured in place by engaging the hook elements 124 and 134 of the auxiliary straps 120 and 130, respectively, with the loop element 106 of the second upper anchor band 96, as best seen in FIG. 9. The auxiliary straps 120 and 130 each are provided with a twist, at 232, to direct the pull of auxiliary straps 120 and 130 more toward the posterior direction so as to provide support for the lower leg 184, and consequently the upper tibia, which braces against anterior subluxation of the tibia.

Figure 10:
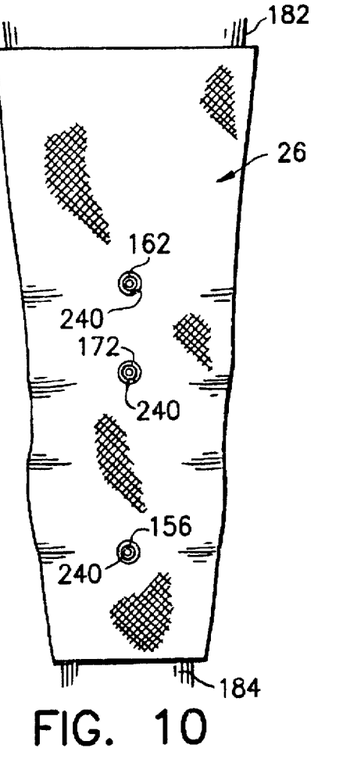
Figure 11:
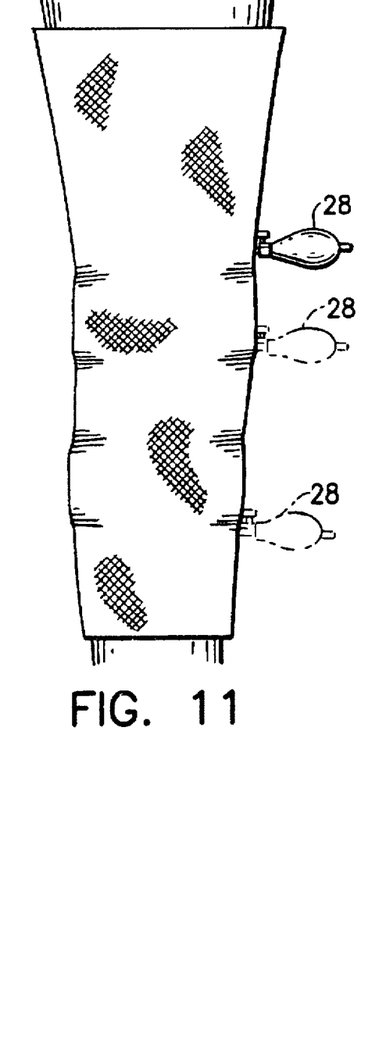
FIG. 11 is a side elevational view similar to FIG. 10, but illustrating another stage of attachment.

Once all of the straps 70, 90, 120 and 130 are in place, as described above, the outer sleeve 26 is located over the support component 22 so as to be placed as shown in FIGS. 10 and 11. Outer sleeve 26 is constructed in the form of a relatively thin sheath of a resiliently expansible material, such as LYCRA, and is slipped, stocking-like, over the support component 22 which has been installed as described above. Apertures 240 in the outer sleeve 26 are registered with respective valves 156, 162 and 172, so that the valves 156, 162 and 172 each extend through the outer sleeve 26 for selective coupling with the air pump 28. The air pump 28 then is employed to inflate the bladders 150, 160 and 170, thereby increasing the grip of the previously located anchor bands 32, 76 and 96 and firmly anchoring the respective anchor bands 32, 76 and 96 in the appropriate location. The firm anchoring of the anchor bands 32, 76 and 96 fixes the placement of the first and second straps 70 and 90 and the first and second auxiliary straps 120 and 130, and secures the support component 22 in place for appropriate bracing of the knee 180. The construction of knee brace 20 enables the separate steps of locating the lower and upper anchor bands 32, 76 and 96, and the several straps 70, 90, 120 and 130 in appropriate placement relative to the knee 180 with ease, and then firmly anchoring the anchor bands 32, 76 and 96 to secure that placement by subsequent inflation of the several inflatable means, while maintaining the combination of flexibility and inextensibility in the straps 70, 90, 120 and 130. In this manner, accuracy is attained with increased ease in the initial location of the knee brace 20 and in the maintenance of that location during use, with increased comfort.

Figure 12:
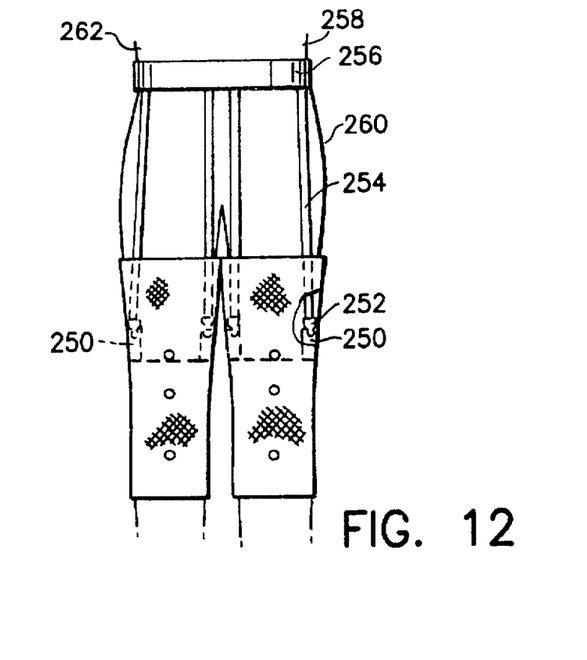
FIG. 12 is a front elevational view showing knee braces attached to a wearer and incorporating supplemental supports.

Turning now to FIG. 12, as an additional feature in assisting in maintaining the knee brace 20 in place at the knee 180, a support tab 250 projects upwardly from each of the terminal segments 74 and 94 of each of the first and second straps 70 and 90, respectively, for engagement by a clip 252 suspended by a tether 254 from a belt 256 at the waist 258 of the body 260 of a wearer 262, to assist in maintaining the support component 22 in place.

Figure 13:
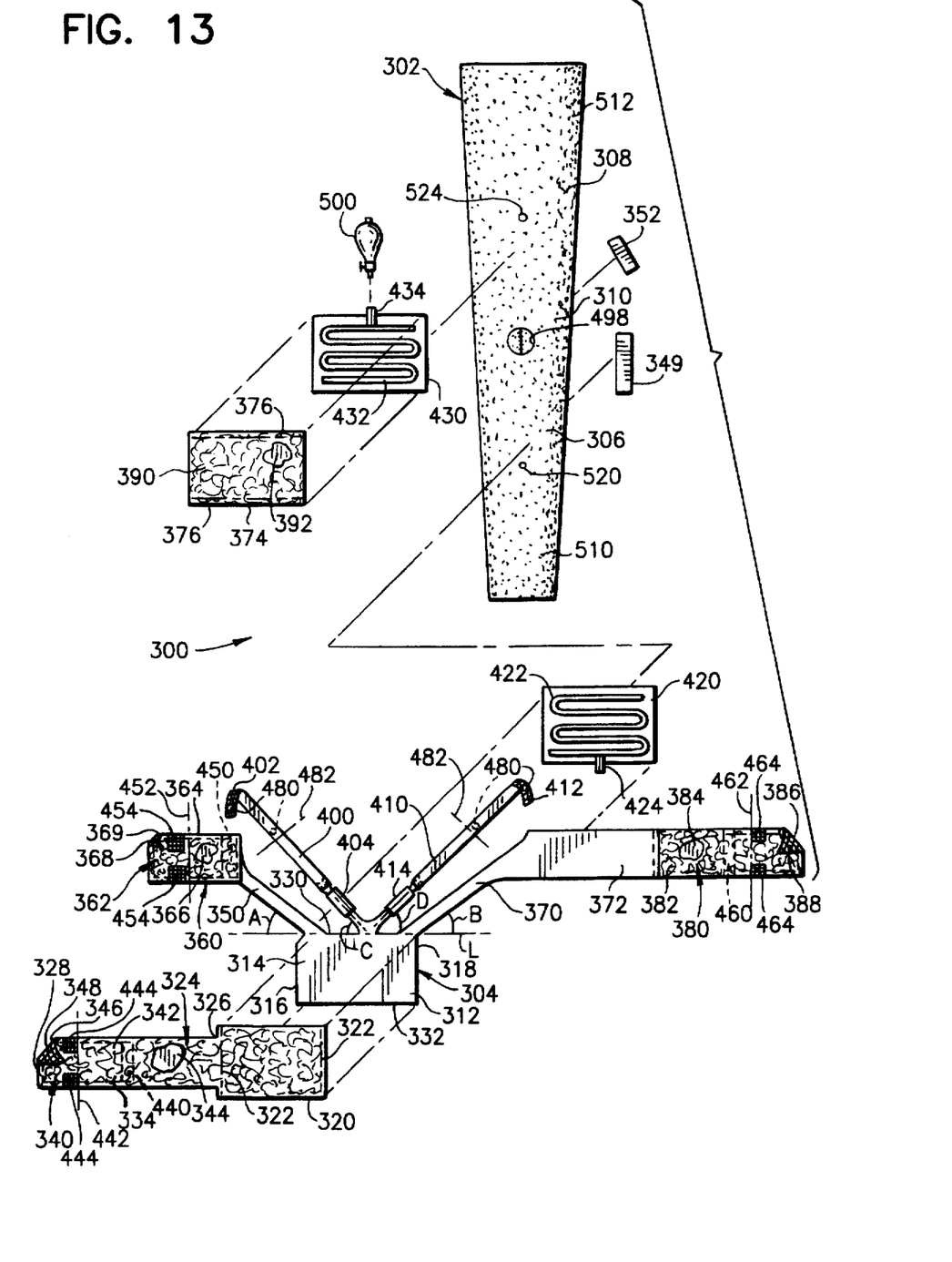
FIG. 13 is a pictorial illustration of component parts of another knee brace constructed in accordance with the present invention.

Another embodiment of the present invention is illustrated in FIGS. 13 through 20. Referring now to FIG. 13, another knee brace constructed in accordance with the present invention is illustrated at 300 and is seen to include a support sleeve 302 and a support component 304. Support sleeve 302 may be constructed of a material similar to that of inner sleeve 24 described above in connection with knee brace 20 and includes a lower tubular portion 306, an upper tubular portion 308, and an intermediate tubular portion 310. Support component 304 includes a member 312 in the form of a relatively thin sheet of flexible and essentially inextensible synthetic polymeric material, such as a commercially available nylon fabric coated on one side with a polyurethane film, the term "essentially inextensible" meaning that the material resists stretching in response to tensile loads, while remaining flexible. Member 312 includes a lower front support in the form of a pad 314 extending in a lateral direction between opposite support ends 316 and 318.

A lower securing element 320 is attached to the front of the lower tubular portion 306, as by stitching along longitudinal lines 322, so as to be affixed permanently to the front of sleeve 302. A lower anchor band 324 extends laterally between band ends 326 and 328 and is attached at end 326 to the lower tubular portion 306 through lower securing element 320, the lower anchor band 324 being unitary with the lower securing element 320. Pad 314 has a laterally extending upper edge 330 and an opposite laterally extending lower edge 332 spaced altitudinally from the upper edge 330. Lower anchor band 324 includes securing means in the form of a securing segment 334 extending laterally from the lower securing element 320 to the end 328 and carrying a hook-and-loop fastener 340 having an elongate loop element 342, extending along a front face 344 of securing segment 334 from the lower securing element 320 to the end 328, and a hook element 346 extending along a rear face 348 of the securing segment 334 from the end 328 toward the end 326 (see FIG. 16). Lower securing element 320 is itself a loop element compatible with the hook-and-loop fastener 340. A suitable hook-and-loop fastener is available under the trademark VELCRO. A lower guide band 349 is attached to the sleeve 302, at the rear of the lower tubular portion 306, as by sewing the lower guide band 349 to the sleeve 302, and the lower anchor band 324 slides between the lower guide band 349 and the sleeve 302 to follow a circular path around the sleeve 302.

A first strap 350 is integral with the pad 314 adjacent the upper edge 330 of the pad 314 and projects from the pad 314 upwardly at an acute angle A to the lateral direction L to extend generally toward the upper tubular portion 308 of the sleeve 302. A first upper guide band 352 is attached to the sleeve 302, at the rear of the upper tubular portion 308 of the sleeve 302 (see FIG. 15), as by sewing the guide band 352 to the sleeve 302. The first guide band 352 guides and supports the first strap 350 along a first helical path 354 around the sleeve 302, with the first strap 350 being slidable between the first guide band 352 and the sleeve 302. A first upper anchor band 360 is integral with the first strap 350 and is spaced away from the upper edge 330 of the pad 314, the first upper anchor band 360 extending laterally for being located along the upper tubular portion 308 of the sleeve 302, as will be described in detail below. A first upper anchor band securing means is provided in the form of a hook-and-loop fastener 362 extending along the first upper anchor band 360, the hook-and-loop fastener 362 having a loop element 364 extending along a front face 366 of the first upper anchor band 360 and a hook element 368 extending along a rear face 369 of the upper anchor band 360 (also see FIG. 16).

A second strap 370 is integral with the pad 314 adjacent the upper edge 330 and projects from the pad 314 upwardly at an acute angle B to the lateral direction L to extend generally toward the upper tubular portion 308 of the sleeve 302. A second upper anchor band 372 is integral with the second strap 370 and is spaced away from the upper edge 330 of the pad 314, the second upper anchor band 372 extending laterally and being located along the upper tubular portion 308 of the sleeve 302 by passing beneath a second upper guide band 374 attached to the front of the upper tubular portion 308 of the sleeve 302, as by sewing the second guide band 374 to the sleeve 302 along lateral lines 376, with the second strap 370 extending along a second helical path 378 around the sleeve 302, the second helical path 378 being opposite to the first helical path 354. The lateral lines 3766 are spaced apart altitudinally to enable the second strap 370 to slide laterally between the second upper guide band 374 and the sleeve 302. Second upper band securing means are provided in the form of a hook-and-loop fastener 380 extending along the second upper anchor band 372, with a loop element 382 at the front face 384 of the second upper anchor band 372 and a hook element 386 at the rear face 388 of the second upper anchor band 372. An upper securing element is shown in the form of a loop element 390 compatible with the hook-and-loop fastener 380 and extending along the front face 392 of the second guide band 374.

A first auxiliary strap 400 is integrated with the pad 314 adjacent the upper edge 330 of the pad 314 and projects from the pad 314 at an acute angle C to the lateral direction L to extend generally toward the upper tubular portion 308 of the sleeve 302. First auxiliary securing means in the form of an elongate hook element 402 compatible with the hook-and-loop fastener 380 extends along the first auxiliary strap 400. A selectively detachable connector 404 connects the first auxiliary strap 400 to the pad 314 so that the first auxiliary strap 400 may be detached and removed selectively from the pad 314, for purposes described below. A second auxiliary strap 410 is integrated with the pad 314 adjacent the upper edge 330 of the pad 314 and projects from the pad 314 at an acute angle D to the lateral direction L to extend generally toward the upper tubular portion 308 of the sleeve 302. Second auxiliary securing means in the form of an elongate hook element 412 compatible with the hook-and-loop fastener 380 extends along the second auxiliary strap 410. A selectively detachable connector 414 connects the second auxiliary strap 410 to the pad 314 so that the second auxiliary strap 410 may be detached and removed selectively from the pad 314, for purposes described below.

Lower inflatable means in the form of a lower bladder 420 having a sinuous internal passage 422 and a valve 424 is affixed to the lower tubular portion 306 of the sleeve 302, interposed between the pad 314 and the sleeve 302, in position to be overlapped by the lower anchor band 324, as will be described below. Upper inflatable means in the form of an upper bladder 430 having a sinuous internal passage 432 and a valve 434 is affixed to the upper tubular portion 308 of the sleeve 302, interposed between the second guide band 374 and the sleeve 302, in position to be overlapped by the first and second upper anchor bands 360 and 372, also as will be described below.

Figures 14, 19, 20:
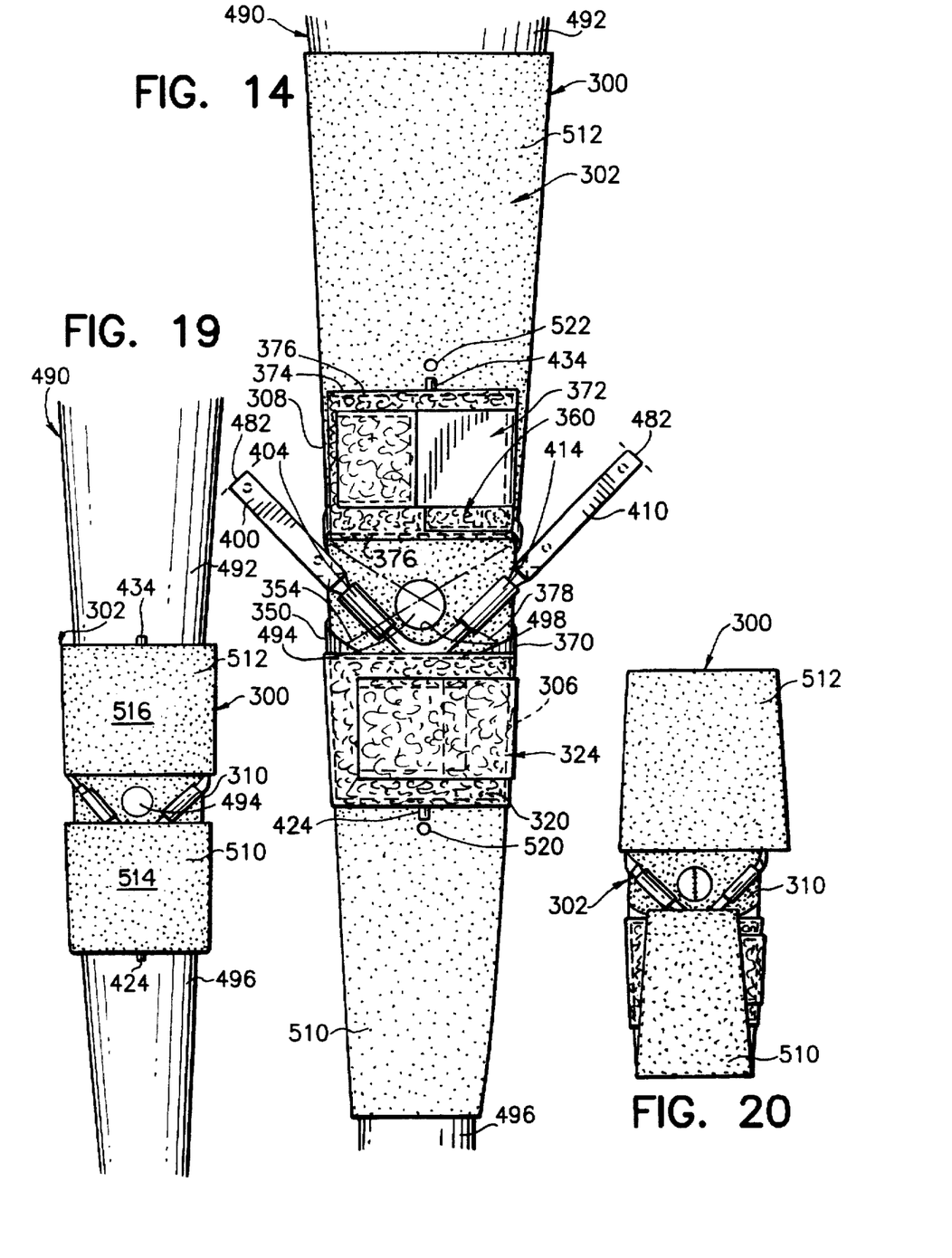
FIG. 14 is a front elevational view showing the knee brace placed upon a leg of a wearer.
FIG. 19 is a front elevational view showing the knee brace placed and fully secured in place upon a wearer.
FIG. 20 is a front elevational view showing the knee brace folded for storage and transportation.
Figure 15:
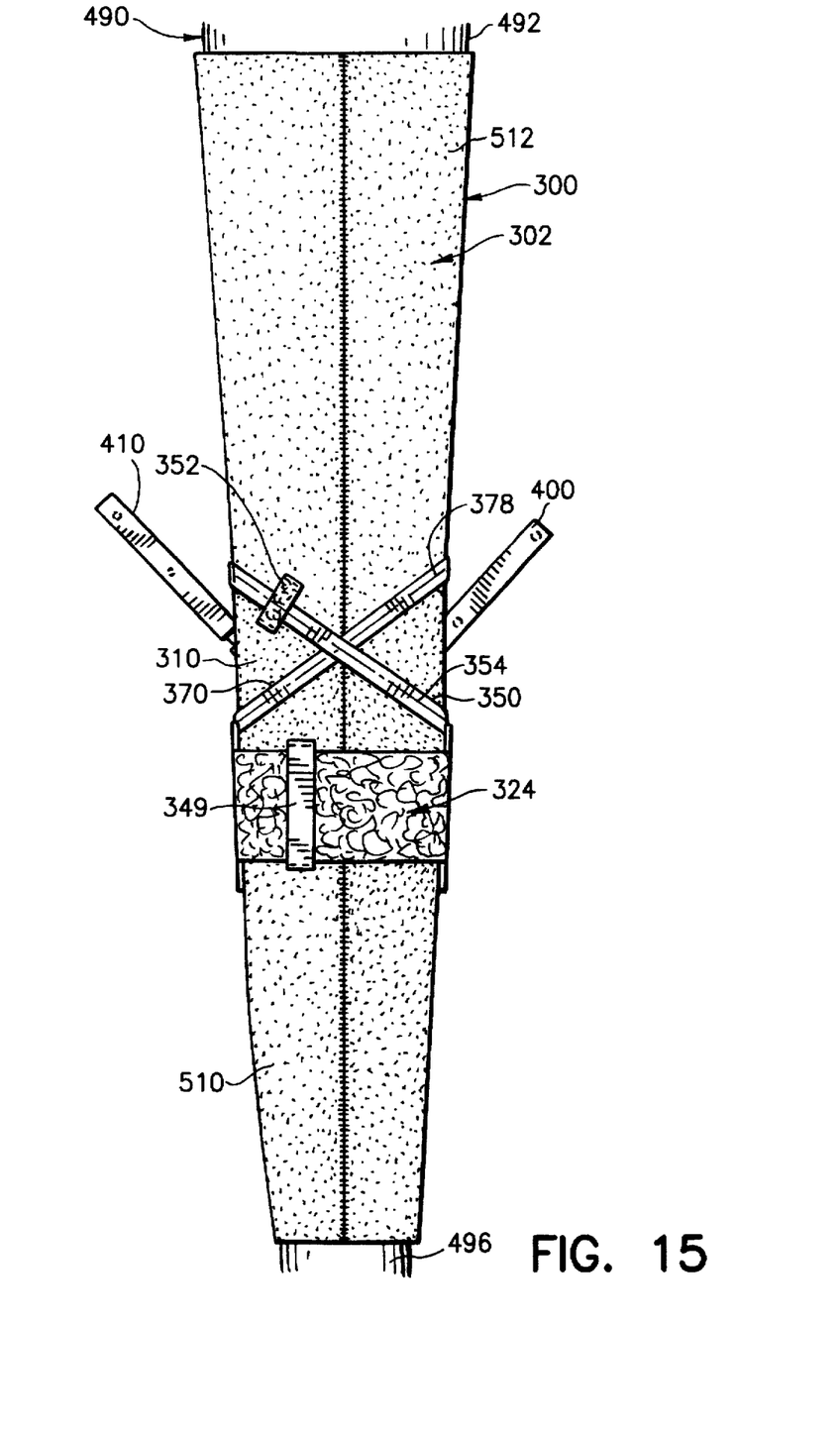
FIG. 15 is a rear elevational view of the depiction in FIG. 14.

In order to enable increased ease in placement of the brace 300 upon a wearer, and to facilitate handling of the brace 300 during storage and transportation, as well as during placement of the brace 300 on a wearer, brace 300 is provided with temporary securing means for temporarily securing the various anchor bands 324, 360 and 362 in position for simplified manipulation of the brace 300. To those ends, a strip 440 carrying loops compatible with hook-and-loop fastener 340 is affixed to the rear face 348 of securing segment 334 of the lower anchor band 324 SO that the lower anchor band 324 is folded along fold line 442 and maintained in the folded configuration by temporary securement of the strip 440 and the hook element 346. Pads 444 carrying hooks compatible with hook-and-loop fastener 340 are placed on the front face 344 of securing segment 334 of the lower anchor band 324 so that the lower anchor band 324, passed beneath the lower guide band 349 and folded upon itself, then can be secured temporarily to the lower securing element 320, as illustrated in FIGS. 14 and 15. In a similar manner, a strip 450 carrying loops compatible with hook-and-loop fastener 362 is affixed to the first upper anchor band 360, enabling the first upper anchor band 360 to be retained temporarily in a folded configuration, folded along fold line 452, and temporarily secured to loop element 364, as seen in FIG. 14, by means of pads 454 carrying hooks and affixed to the front face 3666 of the first upper anchor band 360. Similarly, a strip 460 carrying loops is affixed to the second upper anchor band 372 for retaining the second upper anchor band 372 folded about fold line 462, and pads 464 carrying hooks temporarily secure the folded second upper anchor band 372 to loop element 382, as illustrated in FIG. 14. In addition, each auxiliary strap 400 and 410 includes buttons 480 carrying loops compatible, respectively, with the hook elements 402 and 412 so that each of the auxiliary straps 400 and 410 can be held folded upon itself, along a fold line 482, as shown in FIGS. 14 and 15, thereby covering the hook elements 402 and 412 and rendering the hook elements 402 and 412 benign and inactive during handling of the brace 300.

The above-described construction of brace 300 enables the brace 300 to be placed upon the leg of a wearer with increased ease. Thus, as seen in FIGS. 14 and 15, brace 300 is supplied to the wearer with the lower anchor band 324 and the upper anchor bands 360 and 372 temporarily secured against the sleeve 302, and with the auxiliary straps 400 and 410 inactive. In addition, the straps 350 and 370 already follow the first and second helical paths 354 and 378 around the sleeve 302. The sleeve 302 is then readily slipped over the leg 490 of the wearer, and placed so that the upper tubular portion 308 of the sleeve 302 is over the upper leg 492, adjacent knee joint 494, the lower tubular portion 306 is over the lower leg 496, adjacent the knee joint 494, and the intermediate tubular portion 310 is over the knee joint 494, with an opening 498 in the sleeve 302 registered with the patella of the knee joint 494.

Figure 16:
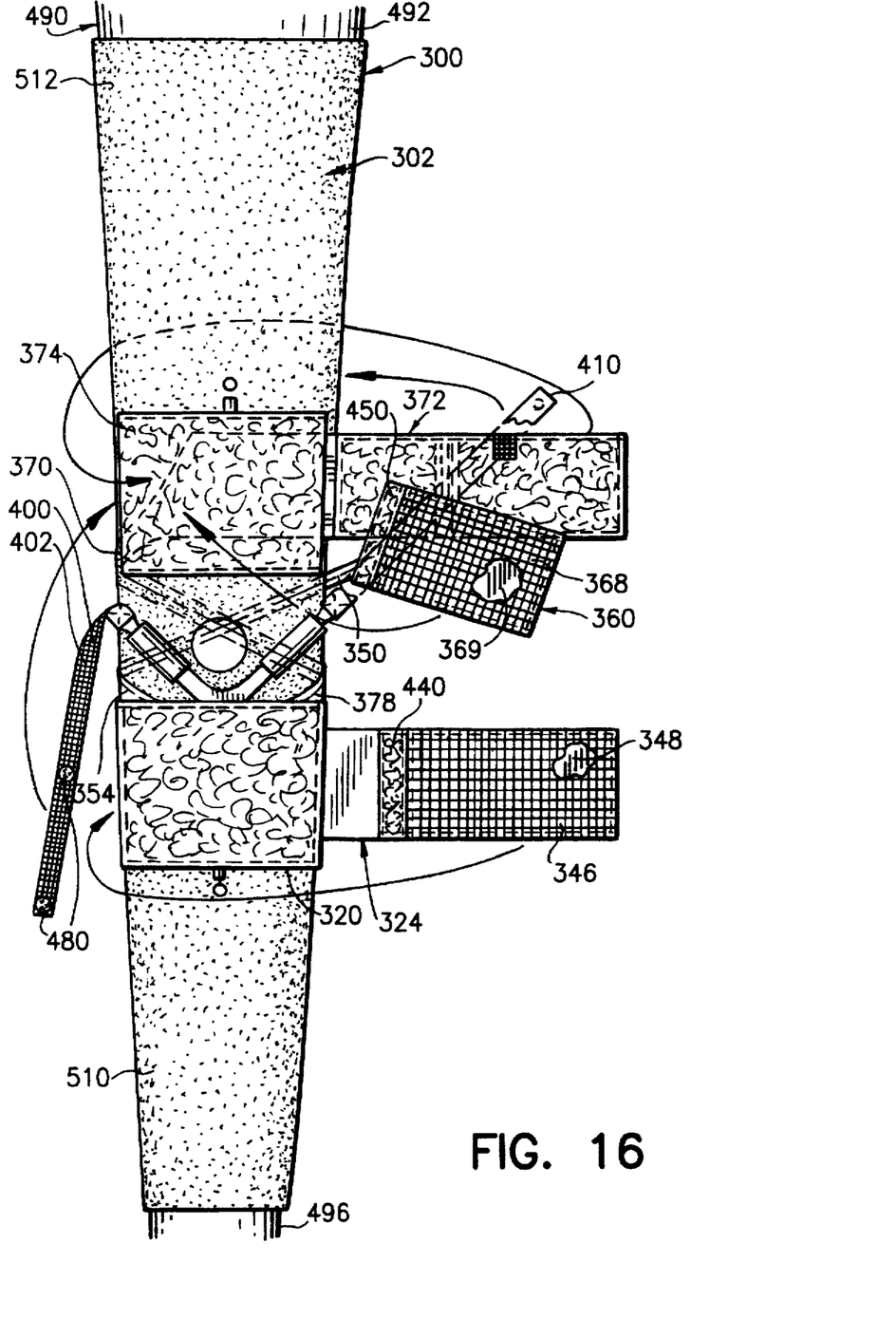
FIG. 16 is a front elevational view similar to FIG. 14, but showing an initial stage of securement.
Figure 17:
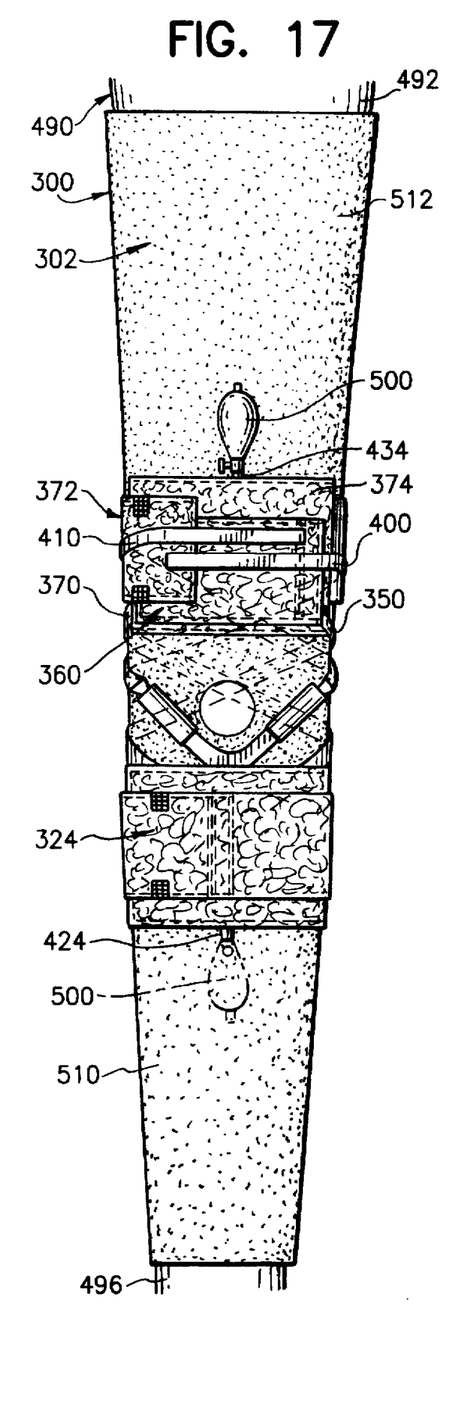
FIG. 17 is a front elevational view showing a further stage of securement.
Figure 18:
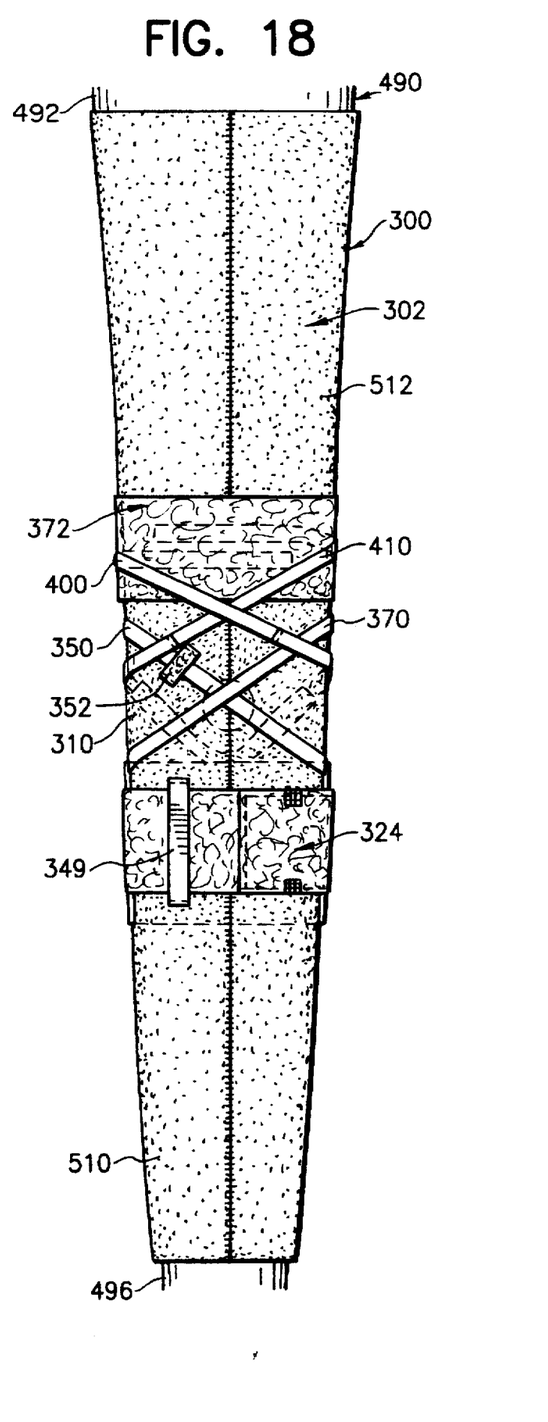
FIG. 18 is a rear elevational view of the depiction in FIG. 17.

Once the brace 300 is in place, as illustrated in FIGS. 14 and 15, the lower anchor band 324 is released from the temporary securement and is wrapped tightly around the lower tubular portion 306 of the sleeve 302, as shown in FIG. 16. Then, the hook element 346 of fastener 340 is secured to one or both of the lower securing element 320 and the loop element 342, depending upon the girth of the lower leg 496, as shown in FIGS. 17 and 18. The first strap 350, which already is routed around the sleeve 302 along the first helical path 354, merely is pulled tight and the first upper anchor band 360 is secured to loop element 390. The second strap 370, which already is routed around the sleeve 302 along the second helical path 378, also is pulled tight and the second upper anchor band 372 is passed over the first upper anchor band 360 and is secured to one or more of the loop element 390, the loop element 364 of the first upper anchor band 360 and the loop element 382 of the second upper anchor band 372, depending upon the girth of the upper leg 492, all as illustrated in FIGS. 17 and 18. It is noted that the second upper anchor band 372 has a greater lateral extent than the first upper anchor band 360 so that the second upper anchor band 372 is wrapped around the sleeve 302, over the first upper anchor band 360. Subsequently, the auxiliary straps 400 and 410 are unfolded and wound around the sleeve 302, passing over the intermediate tubular portion 310 to the upper tubular portion 308, along helical paths, to be affixed over the first and second upper anchor bands 360 and 372, as seen in FIGS. 17 and 18. In some instances, the added support and stability provided by auxiliary straps 400 and 410 is not needed. In such instances, the auxiliary straps 400 and 410 may be detached and removed from pad 314, by selectively detaching the connectors 404 and 414. Alternately, brace 300 can be supplied without auxiliary straps 400 and 410.

Once the lower anchor band 324 and the first and second upper anchor bands 360 and 372 are secured in place, as described above, and the auxiliary straps 400 and 410 are secured in place, if -necessary and present, the lower and upper bladders 420 and 430 are inflated by connecting an air pump 500 to the respective valves 424 and 434 and operating the air pump 500, when connected to each valve 424 and 434, to inflate the respective bladders 420 and 430. As before, inflation of the bladders 420 and 430 will secure the components of the brace 300 in place upon the leg 490 of the wearer for effective support of the weakened knee joint 494.

Returning now to FIG. 14, the sleeve 302 preferably is extended downwardly by the inclusion of a lower tubular extension 510 extending downwardly from the lower tubular portion 306 of the sleeve 302, and is extended upwardly by the inclusion of an upper tubular extension 512 extending upwardly from the upper tubular portion 308 of the sleeve 302. As seen in FIG. 19, upon completion of the placement of the brace 300 upon the leg 490 of the wearer, over the knee joint 494, the lower tubular extension 510 is folded over the lower tubular portion 306 of the sleeve 302, and over the lower anchor band 324, to present a relatively smooth and uncluttered lower exterior surface 514. Likewise, the upper tubular extension 512 is folded over the upper tubular portion 308 of the sleeve 302, and over the first and second upper anchor bands 360 and 372, and over the auxiliary straps 400 and 410, to present a relatively smooth and uncluttered upper exterior surface 516. In this manner, the need for a separate outer sleeve is eliminated.

In order to facilitate the folding of the lower and upper tubular extensions 510 and 512 over the lower and upper tubular portions 306 and 308, as described above, inflation of the lower and upper bladders 420 and 430 may be deferred until after the folding operation. To that end, lower and upper clearance holes 520 and 522 are provided in the sleeve 302 for enabling access to the valves 424 and 432 after the folding over of the lower and upper tubular extensions 510 and 512. Access to the valves 424 and 434 also enables deflation of the lower and upper bladders 420 and 430 for ease of unfolding the lower and upper tubular extensions 510 and 512 when the brace 300 is to be removed from the leg 490.

As seen in FIG. 20, the temporary securement of the lower anchor band 324 to the lower tubular portion 306 of the sleeve 302, and the temporary securement of the first and second upper anchor bands 360 and 372 to the upper tubular portion 308 of the sleeve 302 provides brace 300 with a compact and uncluttered configuration for storage and for ease of handling during transportation. Brace 300 is readily packaged in a form made available for simplified placement on the leg 490 of a wearer, as described above.

It will be seen that the present invention attains the several objects and advantages summarized above, namely: Provides effective support to a weakened knee with minimal interference with the functioning of the knee during normal activity; enables increased ease of placement and securement in appropriate position in relation to the knee, with increased accuracy of placement; provides a secure attachment to the leg for maintaining the brace accurately in place during use; enables ease of attachment and detachment through simplified multiple steps for encouraging proper use; attains a higher degree of comfort both during installation and during use, with ease of adjustment to maintain proper placement as well as comfort; enables ease of storage and transportation, as well as ready proper placement and securement in place; provides a simplified construction which is economical to manufacture and attains reliable performance over an extended service life.

It is to be understood that the above detailed description of preferred embodiments of the invention is provided by way of example only. Various details of design and construction may be modified without departing from the true spirit and scope of the invention, as set forth in the appended claims.

The embodiments of the invention in which an exclusive property or privilege is claimed are defined as follows:

1. A brace to be attached to an upper leg and a lower leg of a body for supporting a weakened knee joint located between the upper leg and the lower leg, the brace comprising:

a sleeve of resilient material for fitting over the knee joint, the sleeve having a lower tubular portion for extending over the lower leg adjacent the knee joint, an upper tubular portion for extending over the upper leg adjacent the knee joint, and an intermediate tubular portion for extending over the knee joint when the sleeve is fitted over the knee joint;

a lower securing element attached to the lower tubular portion of the sleeve;

a lower anchor band attached to the lower tubular portion of the sleeve and extending in a lateral direction between opposite band ends for being located at a location along the lower tubular portion of the sleeve, the lower anchor band including lower band securing means for securing the lower anchor band to the lower securing element in the location along the lower tubular portion of the sleeve;

a lower front support attached to the lower tubular portion of the sleeve, the lower front support extending in the lateral direction between opposite support ends and having a laterally extending upper edge and an opposite laterally extending lower edge spaced altitudinally from the upper edge;

a first strap integral with the lower front support adjacent the upper edge, the first strap projecting from the lower front support upwardly at an acute angle to the lateral direction to extend generally toward the upper tubular portion of the sleeve;

a first guide band attached to the sleeve and guiding the first strap along a first helical path around the sleeve;

an upper securing element attached to the upper tubular portion of the sleeve;

a first upper anchor band integral with the first strap and spaced away from the upper edge of the lower front support, the first upper anchor band extending laterally for being located at a first location along the upper tubular portion of the sleeve, adjacent the intermediate portion of the sleeve, and including first upper anchor band securing means for securing the first upper anchor band to the upper securing element in the first location along the upper tubular portion of the sleeve, with the first strap following the first helical path;

a second strap integral with the lower front support adjacent the upper edge and projecting from the lower front support upwardly at an acute angle to the lateral direction to extend generally toward the upper tubular portion of the sleeve;

a second guide band attached to the sleeve and guiding the second strap along a second helical path around the sleeve, the second helical path being opposite to the first helical path;

a second upper anchor band integral with the second strap and spaced away from the upper edge of the lower front support, the second upper anchor band extending laterally for being located at a second location along the upper tubular portion of the sleeve, adjacent the intermediate portion of the sleeve, and including second upper band securing means for securing the second upper anchor band to the upper securing element at the second location along the upper tubular portion of the sleeve, with the second strap following the second helical path;

lower inflatable means attached to the lower tubular portion of the sleeve in position for being overlapped by the lower anchor band when the lower anchor band is secured to the lower securing element in the location along the lower tubular portion of the sleeve, the lower inflatable means being selectively inflatable when the lower tubular portion of the sleeve and the lower anchor band are located over the lower leg to grip the lower leg and anchor the lower anchor band to the lower leg; and upper inflatable means attached to the upper tubular portion of the sleeve in position to be overlapped by the first and second upper anchor bands when the first and second upper anchor bands are secured to the upper securing element in the respective first and second locations along the upper tubular portion of the sleeve, the upper inflatable means being selectively inflatable when the upper tubular portion of the sleeve and the first and second upper anchor bands are located over the upper leg to grip the upper leg and anchor the first and second upper anchor bands to the upper leg;

the first and second straps being essentially inextensible such that upon anchoring the lower anchor band to the lower leg, the first upper anchor band to the upper leg and the second upper anchor band to the upper leg, with the first and second straps following the respective first and second helical paths, the first and second straps support the weakened knee joint.

2. The invention of claim 1 wherein the lower anchor band is attached to the lower tubular portion of the sleeve at one of the opposite band ends, and the lower securing element is juxtaposed with said one of the opposite band ends.

3. The invention of claim 2 wherein the lower front support is interposed between said one of the opposite band ends and the lower tubular portion of the sleeve.

4. The invention of claim 2 wherein the lower inflatable means is interposed between the lower securing element and the lower tubular portion of the sleeve.

5. The invention of claim 1 wherein the upper inflatable means is interposed between the upper securing element and the upper tubular portion of the sleeve.

6. The invention of claim 5 wherein the upper securing element is juxtaposed with the second guide band.

7. The invention of claim 1 including:

a first auxiliary strap attached to the lower front support adjacent the upper edge of the lower front support and projecting from the lower front support upwardly at an acute angle to the lateral direction to extend generally toward the upper tubular portion of the sleeve for following a first auxiliary helical path around the knee joint, the first auxiliary strap including first auxiliary securing means for securing the first auxiliary strap wrapped around the knee joint, with the first auxiliary strap following the first auxiliary helical path; and a second auxiliary strap attached to the lower front support adjacent the upper edge of the lower front support and projecting from the lower front support upwardly at an acute angle to the lateral direction to extend generally toward the upper tubular portion of the sleeve for following a second auxiliary helical path around the knee joint, the second auxiliary helical path being opposite to the first auxiliary helical path, the second auxiliary strap including second auxiliary securing means for securing the second auxiliary strap wrapped around the knee joint, with the second auxiliary strap following the second auxiliary helical path;

the first and second auxiliary straps being located between the first and second straps.

8. The invention of claim 7 including:

a first selectively detachable connector connecting the first auxiliary strap to the lower front support for selective detachment and removal of the first auxiliary strap from the lower front support; and a second selectively detachable connector connecting the second auxiliary strap to the lower front support for selective detachment and removal of the second auxiliary strap from the lower front support.

9. The invention of claim 1 wherein the first upper anchor band has a first lateral extent, and the second upper anchor band has a second lateral extent greater than the first lateral extent for wrapping the second upper anchor band around the upper leg, over the first upper anchor band.

10. The invention of claim 1 wherein the lower anchor band is attached to the lower tubular portion of the sleeve at one of the opposite ends of the lower anchor band, and the lower anchor band includes lower temporary securing means for temporarily securing the other of the opposite ends of the lower anchor band adjacent the one of the opposite ends during storage, transportation and placement of the sleeve over the knee joint.

11. The invention of claim 1 including a further guide band attached to the lower tubular portion of the sleeve and guiding the lower anchor band around the lower tubular portion of the sleeve.

12. The invention of claim 1 including first upper temporary securing means for temporarily securing the first upper anchor band to the upper tubular portion of the sleeve during storage, transportation and placement of the sleeve over the knee joint, and second upper temporary securing means for temporarily securing the second upper anchor band to the upper tubular portion of the sleeve during storage, transportation and placement of the sleeve over the knee joint.

13. The invention of claim 1 wherein the sleeve includes a lower tubular extension extending downwardly beyond the lower tubular portion of the sleeve for folding upwardly over the lower anchor band and over the lower tubular portion of the sleeve subsequent to anchoring the lower anchor band to the lower leg.

14. The invention of claim 1 wherein the sleeve includes an upper tubular extension extending upwardly beyond the upper tubular portion of the sleeve for folding downwardly over the first upper anchor band and the second upper anchor band and over the upper tubular portion of the sleeve subsequent to anchoring the first upper anchor band and the second upper anchor band to the upper leg.

15. The invention of claim 1 wherein the sleeve includes a lower tubular extension extending downwardly beyond the lower tubular portion of the sleeve for folding upwardly over the lower anchor band and over the lower tubular portion of the sleeve subsequent to anchoring the lower anchor band to the lower leg, and an upper tubular extension extending upwardly beyond the upper tubular portion of the sleeve for folding downwardly over the first upper anchor band and the second upper anchor band and over the upper tubular portion of the sleeve subsequent to anchoring the first upper anchor band and the second upper anchor band to the upper leg.

* * * * *